US009008389B2

(12) United States Patent
Williams

(10) Patent No.: US 9,008,389 B2
(45) Date of Patent: Apr. 14, 2015

(54) SYSTEM AND METHOD FOR DETERMINING THE AMOUNT OF VITAMIN D GENERATED BY A USER

(71) Applicant: Robert D. Williams, Los Angeles, CA (US)

(72) Inventor: Robert D. Williams, Los Angeles, CA (US)

( * ) Notice: Subject to any disclaimer, the term of this patent is extended or adjusted under 35 U.S.C. 154(b) by 20 days.

(21) Appl. No.: 14/039,571

(22) Filed: Sep. 27, 2013

(65) Prior Publication Data

US 2014/0093148 A1    Apr. 3, 2014

Related U.S. Application Data

(60) Provisional application No. 61/707,161, filed on Sep. 28, 2012.

(51) Int. Cl.
| | |
|---|---|
| *G06K 9/00* | (2006.01) |
| *G06T 7/00* | (2006.01) |
| *A61B 5/00* | (2006.01) |
| *G06Q 50/22* | (2012.01) |

(52) U.S. Cl.
CPC ................ *G06T 7/0016* (2013.01); *A61B 5/00* (2013.01); *G06Q 50/22* (2013.01)

(58) Field of Classification Search
CPC ... G06T 7/0016; G06T 7/0014; G06T 7/0012; G06T 2207/30004; G06T 2207/30088
See application file for complete search history.

(56) References Cited

U.S. PATENT DOCUMENTS

| | | | | | |
|---|---|---|---|---|---|
| 4,230,701 | A | * | 10/1980 | Holick et al. | 514/167 |
| 5,776,461 | A | * | 7/1998 | Pillai et al. | 424/401 |
| 5,883,740 | A | * | 3/1999 | Chubb et al. | 359/350 |
| 6,452,188 | B1 | * | 9/2002 | Chubb | 250/372 |
| 6,521,608 | B1 | * | 2/2003 | Henner et al. | 514/167 |
| 6,734,440 | B2 | * | 5/2004 | Questel et al. | 250/474.1 |
| 2002/0115957 | A1 | * | 8/2002 | Sun et al. | 604/20 |
| 2004/0149921 | A1 | * | 8/2004 | Smyk | 250/372 |
| 2008/0069925 | A1 | * | 3/2008 | Vieth et al. | 426/72 |
| 2010/0226946 | A1 | * | 9/2010 | Alberts | 424/401 |
| 2011/0020252 | A1 | * | 1/2011 | Shantha et al. | 424/59 |
| 2011/0052567 | A1 | * | 3/2011 | Petkovich et al. | 424/130.1 |
| 2011/0191272 | A1 | * | 8/2011 | McGuire | 706/11 |

* cited by examiner

*Primary Examiner* — Manav Seth
(74) *Attorney, Agent, or Firm* — Locke Lord LLP; Howard M. Gitten

(57) ABSTRACT

A portable system for determining the amount of Vitamin D generated by a user includes a computer processing unit. A database communicates with the central processing unit and stores body type information regarding a user to be monitored by the system. A geographic positioning system sensor communicates with the computer processing unit for determining a geographic location of the system. The central processing unit determines a skin darkness, and a sun intensity as a function of the output of the geographic sensor to calculate a real time Vitamin D manufactured amount for the user as a function of the body type data, skin darkness and an amount of skin exposed, and displaying an accumulated Vitamin D manufactured amount for a selected time period at a display.

22 Claims, 3 Drawing Sheets

SYSTEM AND METHOD FOR DETERMINING THE AMOUNT OF VITAMIN D GENERATED BY A USER

CROSS REFERENCE TO RELATED APPLICATION(S)

This application claims priority to U.S. Provisional Patent Application No. 61/707,161, filed Sep. 28, 2012, the contents of which are incorporated herein by reference.

BACKGROUND OF THE INVENTION

This invention is directed to a device for determining the amount of Vitamin D generated by a person and a current Vitamin D level for that person, and more particularly, a portable device for determining in real time actual generation of Vitamin D for that person as a function of user physical characteristics and sun exposure.

Maintaining proper Vitamin D levels is absolutely critical to each and every person's health. Vitamin D is required for strong bones as it helps the body use calcium found in the diet. Vitamin D deficiencies have been associated with increased risk of death from cardiovascular disease, cognitive impairment in older adults, severe asthma in children, cancer, and rickets. Conversely healthy amounts of Vitamin D may act as a prevention and treatment of conditions including diabetes, hypertension, glucose intolerance and multiple sclerosis.

In a normal state, the body is always deficient in Vitamin D. Therefore, humans must get Vitamin D from other sources, such as certain fruits and vegetables. However, the body also manufactures Vitamin D when skin is exposed to sunlight. Therefore, Vitamin D deficiency often occurs where a person does not get sufficient exposure to sunlight.

Determining the current amount of Vitamin D in the system of a user, short of continuous blood testing, has for centuries, been hit or miss guesswork as a function of "knowing your own body." The factors going into determining the amount of Vitamin D manufactured by the body is complex, and at a minimum, are a function of body type characteristics, the time of sun exposure, and the intensity of the sun. However, all of these factors are difficult to determine and subject to self-reporting errors as reporting the intensity of the sun, and even some body type characteristics can be a subjective process.

Furthermore, because sun intensity changes with latitude and the seasons, the body manufactures different amounts of Vitamin D from season to season. Additionally, a person in the tropics manufacturers much more Vitamin D, all things being equal, than someone in New York or London. Therefore, it is difficult for a user to adopt a strategy which contains an appropriate level Vitamin D year round.

There are web based tools for approximating daily Vitamin D manufacture that require a user to input all the information such as exposure time of day, exposure duration, location of the sun, and other factors such as skin darkness, height, weight and amount of skin exposed to the sun. The web based calculators then calculate a predicted personal Vitamin D manufacturing amount for that session. These prior art devices have been satisfactory, however they suffer from the disadvantage that they are prone to self-reporting error. Often these determinations are made at a home based computer long after exposure has occurred and inaccurate inputs are provided as a result of faulty memory. Additionally, these calculators only operate on a daily basis and the user must then manually determine overall Vitamin D exposure over a series of sessions and whether they are achieving desired levels across several sessions.

Accordingly, a system and method for determining the amount of Vitamin D manufactured by a person which overcomes the shortcomings of the prior art is desired.

BRIEF SUMMARY OF THE INVENTION

A portable device for determining Vitamin D manufactured by a person includes a database, a computer processing unit, and a global positioning system (GPS) sensor. User body type characteristics are stored in the database. A picture of the user is taken. The computer processing unit determines a skin darkness as a function of the picture. An amount of skin exposed may also be input or determined from a photograph as contrasted to clothing. The GPS sensor provides a location input to the computer processing unit, the computer processing unit determines a global position, and a sun intensity index, as known in the art, for the determined global position. A clock provides a clock input to the computing device to calculate a time duration corresponding to sun exposure, the computer processor determining an amount of Vitamin D manufactured by the user during the calculated time period and displaying that amount and storing the amount in the database.

In another preferred embodiment, the computing device accumulates the calculated Vitamin D manufacturing level for two or more successive time durations to provide one of an average daily Vitamin D level, and a cumulative Vitamin D level. The system uses the determination of manufactured Vitamin D to calculate a current Vitamin D level.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

The amount of Vitamin D any person is generating at any one time as a function of sun exposure is dependent upon a number of variables, only one of which is the position of the sun in the sky, and the intensity of the sun, as measured by the UV index. Basic factors such as user height, weight, age, and skin darkness, latitude, altitude and the amount of exposed skin (as it follows that a fully clothed person has less exposure to the sun at the same geographic position than a person in a bathing suit) need to be accounted for.

Figure 1:
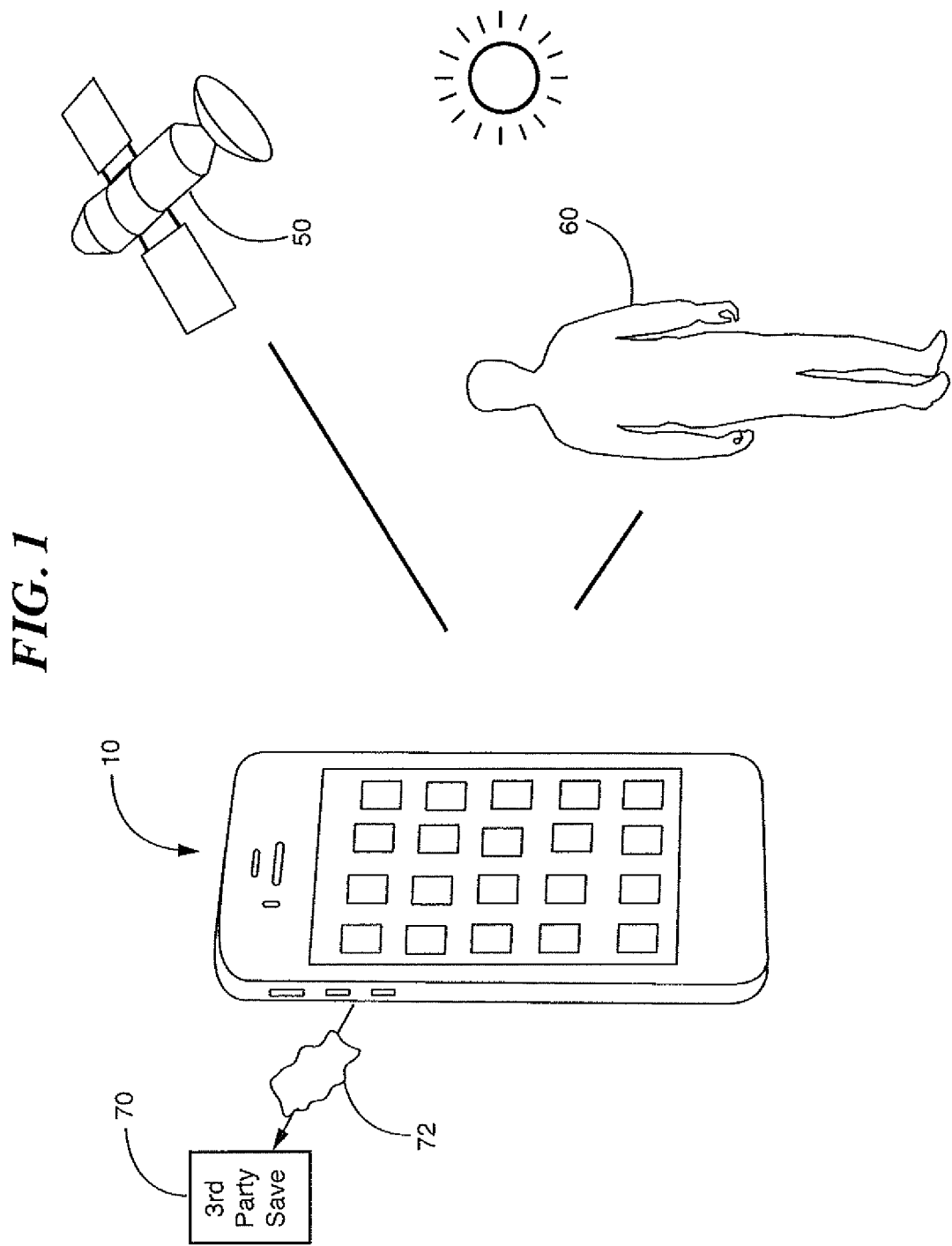
FIG. 1 is a schematic diagram of the environment for a system for determining the amount of Vitamin D generated by a user in accordance with the invention.
Figure 2:
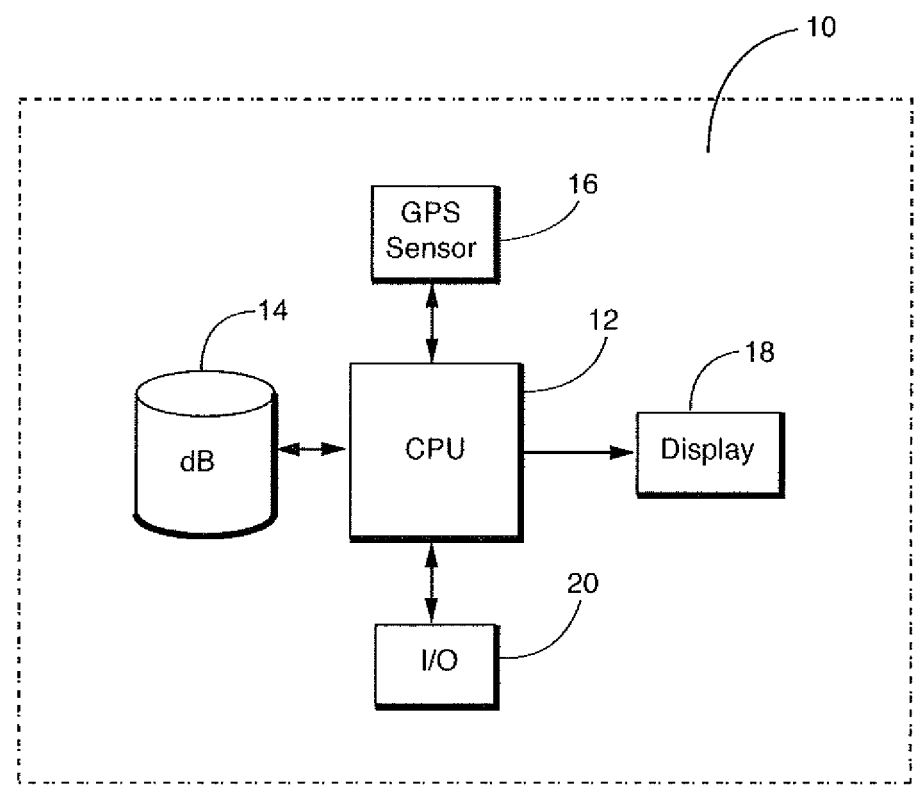
FIG. 2 is a block diagram of a system for computing the amount of Vitamin D in accordance with the invention.

Reference is made to FIGS. 1 and 2 in which a system, generally indicated as 10 is provided for enabling a user to determine, in real time, an amount of Vitamin D manufactured by their body over a duration of time during which they are exposed to the sun. System 10 includes a computer processing unit (CPU) 12 and a database 14 for storing data about the user 60. CPU 12 communicates with, and operates on data stored in, database 14. Database 14 initially stores some body characteristic of user 60, which a user may accurately and easily input, such as height, weight and age. Database 14 may also store instructions for corrective action.

CPU 12 communicates with an input/output device 20 to enable the receipt of instructions and data from user 60. Input/output 20 may also include memory input such as a flash drive, a camera, or any other device capable of capturing data and importing the data to CPU 12 as known in the art. Input/output 20 may be a keyboard, a camera, a speaker, a microphone, or other input or output devices as known in the art. So by way of example, characteristics regarding user 60 may be input at a keyboard, by speaking into a microphone, downloaded from a flash drive, or determined from a digital image photograph. CPU 12 also may provide an output to a display 18 for displaying instruction prompts and results to user 60 during the process described below.

System 10 also includes GPS sensor 16 capable of communicating with GPS satellite 50 as is known in the art and then providing a global position output to CPU 12 for determining the location of system 10. As will be described below, by using GPS sensor 16, determining factors such as longitude, latitude, and altitude, which are more subjective determinations, for an unaided user 60 become more objective. As a result, system 10 is able to make a more accurate determination for key inputs for determining sun intensity during exposure.

System 10 is a portable device. In a preferred but non-limiting embodiment, system 10 is a smartphone in which input/output 20 and display 18 may be combined into a single display having a graphical user interface (GUI) at display 18. However, portable system 10 may be a tablet, or laptop sized computer.

Reference is now more particularly made to FIG. 1 in which the operational environment of system 10 is provided. System 10 utilizes GPS sensor 16 to communicate with GPS satellite 50 as known in the art. Furthermore, as needed, CPU 12 may communicate with a third party data source 70, such as a weather service, or the like across the internet 72, by cellular communication, or the like as known in the art to obtain data for sun intensity as measured by the UV Index in a non-limiting, exemplary embodiment, for a determined geographic location.

Figure 3:
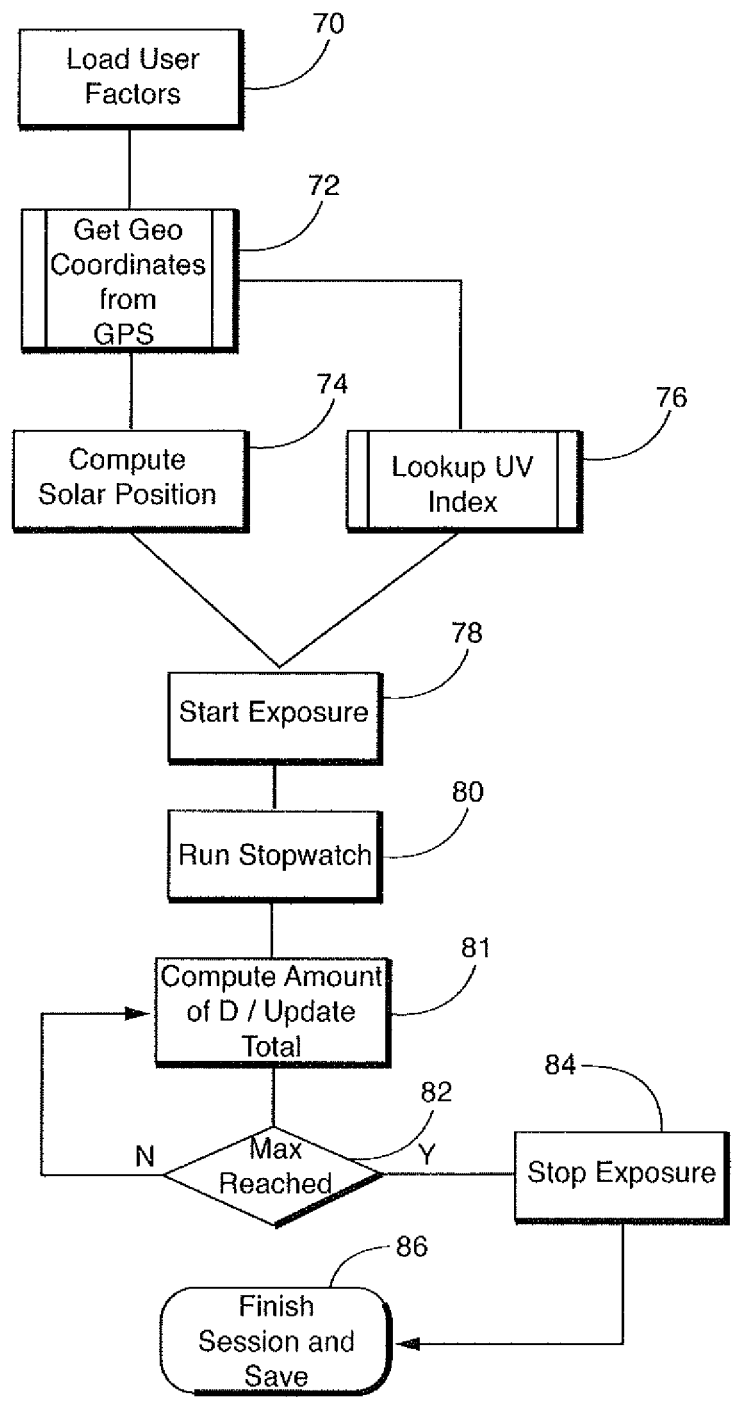
FIG. 3 is a flow chart of the operation of the system in accordance with the invention.

Reference is now made to FIG. 3 in which operation of system 10 is provided. As part of an initialization process, user 60 inputs to system 10 at input/output 20 the quantifiable factors such as height, weight and age. CPU 12 stores this data in database 14. Utilizing a camera version of input/output 20 of system 10, the user takes a picture of their skin. CPU utilizing a digital image and a color comparison algorithm determines a skin darkness factor and stores the skin darkness factor in database 14. Alternative inputs for skin darkness may include a user description in response to a 1-10 scale, 1 corresponding to light skin, burns easily, to 10 black skin, does not burn easily. Additionally the user may be prompted with a photograph corresponding to each level of skin color to select the darkness closest to their actual skin.

In a step 72, CPU 12 operates on inputs from GPS sensor 16 which utilizes GPS satellite 50 to determine the current geographical coordinates (longitude, latitude, altitude) of system 10. In a step 74, given the geographical position as determined, and the time of day as determined from a clock operating within CPU 12 as known in the art, CPU 12 computes a solar position for the geographic coordinates and time of day.

In a step 76, CPU 12 determines a sun intensity. In one exemplary, non-limiting embodiment, the UV index may be used. This may be done by means of a lookup table stored in database 14, by interrogating third party database source 70, such as a weather bureau, using the geographic position information, or performing the same calculation necessary to create the lookup table or the data stored at third party source 70 as a function of geographic position.

The user also inputs a percentage of skin exposed to the sun (exposed skin/total skin area) at input/output 20 determined either by a user input at input/output 20 or by processing a photograph (digital image) of the user and determining the amount of exposed skin the photograph.

Once exposed to the sun, user 60, in a step 78, activates a start input at input/output 20 causing CPU 12 to begin a running elapsed time clock as a stopwatch in step 80. CPU 12 calculates a manufactured Vitamin D amount as a function of each of the body type factors discussed above, the determined skin darkness, the determined percentage and sun intensity.

CPU 12 calculates Vitamin D manufacturing in real time and may store the calculated Vitamin D value at predetermined time intervals in database 14. CPU 12 also calculates a cumulative manufactured amount over a predetermined or running time period. In the simplest form, this may be calculated as the area under the curve as a function of time for the real time Vitamin D amount manufactured or merely a sum of each calculation during the duration as stored in database 14.

As known in the art, while the current level of Vitamin D in the bloodstream and body of the user needs to be replenished on an ongoing basis, it does not necessarily return to zero. Furthermore, food supplementation of Vitamin D level can contribute to a current level, although not to the extent that exposure to the sun contributes to a current level. By way of example, a cup of fortified milk has the same Vitamin D contribution as one minute of noontime sun for a fair skinned user. Therefore, in order to calculate a current Vitamin D level, CPU 12 prompts the user at display 18 to enter, at input/output 20, an amount of various Vitamin D rich foods that have been consumed during a last meal. As a function of look-up tables, third party sources 70 or the like, CPU 12 determines the contribution of such consumption to a current Vitamin D level and for accumulation purposes, treats those levels as manufactured Vitamin D.

The body has a capacity to store excess amounts of Vitamin D. Accordingly, the amount of Vitamin D manufactured in an earlier period, when not fully used, will have a bearing on the determination of a current Vitamin D level of the user. Accordingly, to calculate a Vitamin D level, CPU determines the current level as a function of the real time Vitamin D manufacturing calculation and an accumulated value as stored in database 14. It should also be understood that CPU 12 determines an amount of consumption of Vitamin D by the user so that CPU 12 determines a running accumulation value as manufactured Vitamin D manufactured earlier is more likely to have been consumed than recently manufactured Vitamin D and different weights are given accordingly.

In a step 82, it is determined whether or not a maximum exposure to the sun and/or maximum amount of Vitamin D manufactured for a particular user on a particular day has been reached. This may be a function of the UV index, amount of skin exposed, and skin darkness, all of which are contributing factors to Vitamin D manufacture, sun burn, wrinkling, and/or skin cancer. If it is determined in step 82 that the maximum has not been reached, then the process returns to step 81 and the computation continues. If the maximum has been reached, then exposure should be stopped and a warning will be displayed at display 18 to tell the user that they have reached an exposure limit, and they are prompted to stop the session by inputting a stop command which finishes the calculation. CPU 12 saves the accumulated Vitamin D creation value in database 14.

System 10 computes the Vitamin D being generated by accounting for all the above named conditions which either increase or decrease the rate at which the body produces Vitamin D. This is done by assigning different weightings to each of the inputs. By way of example, a pale skin person generates Vitamin D six times faster than a person with dark or black skin. CPU 12 utilizes weighting difference in step 82 to determine a maximum threshold. CPU 12, utilizing a lookup table stored in database 14 may calculate a required amount of Vitamin D as a function of the body type characteristics of user 60.

Because Vitamin D levels must be maintained year round, accumulating an overall Vitamin D level, as taught above, enables a user to plan for changes in season or even changes in location to prevent a normal deficiency as a function of reduced sunlight from becoming a dangerous deficiency. This allows user 60 to take corrective action. Accordingly, in one embodiment of the invention system 10 may be used for preventive maintenance to prevent shortfalls.

As system 10 determines a projected shortfall as a function of environmental conditions of user 60, CPU 12 calculates an amount of Vitamin D required in a time period to prevent normal deficiencies from becoming serious, and will select corrective action instructions stored in database 14; such as a minimum amount of sun time required in a predetermined time period, or a list of foods or nutraceuticals rich in Vitamin D. These instructions would be displayed at display 18.

By utilizing a mobile device which makes use of actual calculated latitude, longitude, altitude, and skin darkness, and calculates an actual experienced sun intensity, a better predictor of Vitamin D manufacturing within the user body is provided. The amount of human error, based upon inputs after the fact, is significantly reduced and/or eliminated. Furthermore, by utilizing the mobile device, and storing results in the database, the user may readily reference their overall Vitamin D levels from sun exposure, and compare the known monthly or weekly requirements to actual results.

Thus, while there have been shown, described and pointed out, novel features of the present invention as applied to preferred embodiments thereof, it will be understood that various omissions and substitutions and changes in the form of detail are contemplated to the disclosed invention which may be made by those skilled in the art without departing from the spirit and scope of the invention. It is the intention therefore to be limited only as indicated by the scope of claims appended hereto. It is also to be understood that the following claims are intended to cover all the generic and specific features of the invention herein described and all statements of the scope of the invention, which as a matter of language, might be said to fall therebetween.

What is claimed is:

1. A portable system for determining the amount of Vitamin D generated by a user comprising:
   a computer processing unit;
   a database communicating with the central processing unit, the database storing body type information regarding a user to be monitored by the system;
   a geographic positioning system sensor communicating with the computer processing unit for determining a geographic location of the portable system; and
   the central processing unit determining a skin darkness value as a function of an input, and a sun intensity as a function of the geographic position determined by the geographic positioning system sensor; the central processing unit calculating a Vitamin D manufactured amount for the user as a function of the body type information, a sun intensity value, the skin darkness value and an amount of skin exposed.

2. The portable system of claim 1, further comprising a display, the central processing unit communicating with the display to display the amount of Vitamin D manufactured by the user.

3. The portable system of claim 1, further comprising a clock for outputting a clock signal, the central processing unit receiving the clock signal and determining a duration of exposure to the sun by the user.

4. The portable system of claim 1, wherein the computer processing unit stores the amount of Vitamin D manufactured during one or more time intervals in the database, and determines an accumulated Vitamin D manufactured amount as a function of the stored amount.

5. The portable device of claim 4, wherein the computer processing unit determines a current Vitamin D level of a user as a function of at least the stored amount.

6. The portable system of claim 1, further comprising a camera, a central processing unit determining the skin darkness as a function of an image of the user input at the camera.

7. The portable system of claim 1, further comprising an input for receiving a manual input of the skin darkness value.

8. The portable system of claim 6, wherein the central processing unit determines an amount of skin exposed as a function of the image captured at the camera.

9. The portable system of claim 1, wherein the body type information includes at least one of height, weight and age.

10. The portable system of claim 1, wherein the computer processing unit communicates with a third party data source and determines the sun intensity value by requesting a UV index at the third party source as a function of the geographic location of the portable system.

11. The portable system of claim 1, wherein a computer processing unit calculates a cumulative value of Vitamin D manufactured over a time period.

12. A method for determining the amount of Vitamin D generated by a user comprising the steps of:
   providing a portable computer processing unit at a location;
   providing a body type information for the user to the central computer processing unit;
   the portable computer processing unit determining a geographic position of the computer processing unit at the location;
   the portable computer processing unit determining a sun intensity as a function of the geographic position;
   the portable computer processing unit determining a skin darkness value; and
   determining, by the portable computer processing unit, an amount of a Vitamin D manufactured for the user as a function of the body type information, the sun intensity, the skin darkness value and a percentage of skin of the user exposed during a predetermined time period.

13. The method of claim 12, further comprising the steps of the computer processing unit displaying the amount of Vitamin D manufactured by the user.

14. The method of claim 12, further comprising the steps of the central processing unit receiving a clock signal and determining a duration of exposure to the sun by the user.

15. The method of claim 12, further comprising the steps of the computer processing unit storing the amount of Vitamin D manufactured in a database, and determining an accumulated Vitamin D manufactured amount.

16. The method of claim 15, further comprising the step of the computer processing unit determining a current level of Vitamin D for the user as a function of at least the stored amount of Vitamin D.

17. The method of claim 12, further comprising the steps of taking an image of the user with a camera, inputting the image to the central processing unit, the central processing unit determining the skin darkness as a function of the image of the user.

18. The method of claim 12, further comprising the steps of manually inputting of the skin darkness.

19. The method of claim 17, further comprising the steps of the central processing unit determining an amount of skin exposed as a function of the image input from the camera.

20. The method of claim 12, wherein the body type information includes at least one of height, weight and age.

21. The method of claim 12, further comprising the steps of the computer processing unit communicating with a third party data source and determining the sun intensity by requesting a UV index from the third party source as a function of the geographic location of the portable system.

22. The method of claim 12 wherein the computer processing unit calculates a cumulative value of Vitamin D manufactured over a time period.

* * * * *